United States Patent [19]

Typpo

[11] 4,225,243
[45] Sep. 30, 1980

[54] GAS MEASURING APPARATUS WITH STANDARDIZATION MEANS, AND METHOD THEREFOR

[75] Inventor: Pekka M. Typpo, Cupertino, Calif.

[73] Assignee: Measurex Corporation, Cupertino, Calif.

[21] Appl. No.: 919,237

[22] Filed: Jun. 26, 1978

[51] Int. Cl.³ .................... G01N 21/25; G01N 21/00
[52] U.S. Cl. .................... 356/409; 356/439; 356/440
[58] Field of Search .............. 356/437, 438, 439, 440, 356/409; 250/573

[56] References Cited

U.S. PATENT DOCUMENTS

| | | | |
|---|---|---|---|
| 1,969,626 | 8/1934 | Simon et al. | 356/438 |
| 3,895,233 | 7/1975 | Boll et al. | 356/437 |

FOREIGN PATENT DOCUMENTS

| | | | |
|---|---|---|---|
| 2430672 | 1/1976 | Fed. Rep. of Germany | 356/440 |
| 2713637 | 10/1977 | Fed. Rep. of Germany | 356/312 |
| 1327377 | 8/1973 | United Kingdom | 356/438 |

*Primary Examiner*—Vincent P. McGraw
*Attorney, Agent, or Firm*—Ronald L. Yin

[57] ABSTRACT

An apparatus and a method for standardizing a gas measuring device has a source capable of emitting a beam of radiation aligned to impinge a detector. A housing means encloses the beam. The housing means has a plurality of apertures permitting the gas to enter the housing means, to intercept the beam, and to exit from the housing means. The device further comprises means for closing the apertures and a means for purging said gas from the housing means.

5 Claims, 5 Drawing Figures

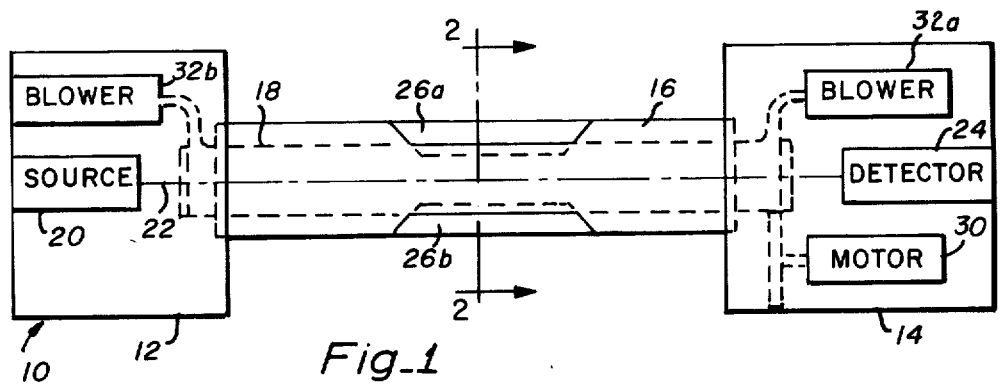
Fig_1
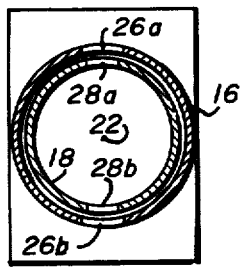
Fig_2A
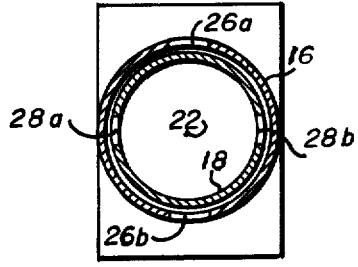
Fig_2B
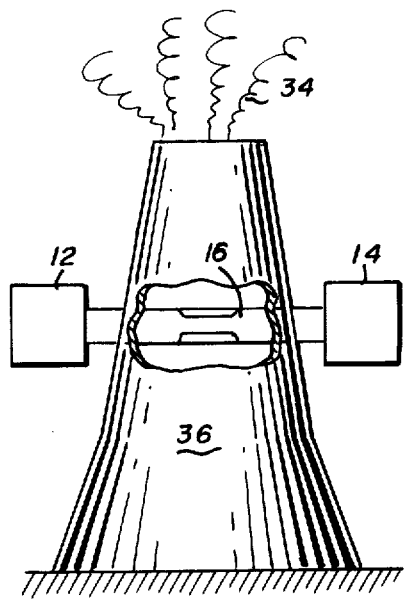
Fig_3
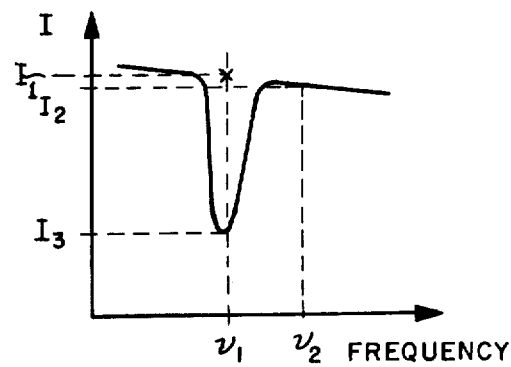
Fig_4

GAS MEASURING APPARATUS WITH STANDARDIZATION MEANS, AND METHOD THEREFOR

BACKGROUND OF THE INVENTION

1. Field of Invention

The present invention relates to an apparatus and a method for measuring the amount of gas. The present invention also relates to a standardization means for such a gas measuring device. Typically, these gases are the exhaust gases, emitted through stacks, produced as a result of combustion.

2. Prior Art

Gas measuring apparatus for monitoring the output of combustion at the stack is well known, see for example U.S. Pat. No. 4,076,425. Typically, these devices operate in harsh environments and in locations that are not easily accessible. Some of the problems, caused thereby, are: lamp aging, drift in electronics and dirt build-up on the window. Thus, to operate effectively, i.e. maintain accuracy and repeatability, these devices must have self-contained standardization means.

Heretofore, one standardization means is described in U.S. Pat. No. 3,836,237. That reference teaches, inter alia, the use of air curtains to keep windows clean. However, despite this practice of air curtains, dirt does build up on the window and must be accounted for in the standardization process. U.S. Pat. Nos. 3,838,925 and 4,076,425 teach the use of alternative optical paths to correct for lamp aging and drift in electronics. These references, however, do not teach the correction of other factors, such as dirt on the windows.

SUMMARY OF THE INVENTION

A gas measuring apparatus comprises a source capable of emitting a beam of radiation. The beam is aligned to impinge a detector. A housing means encloses the beam. The housing means has a plurality of apertures permitting the gas to enter the housing means, intercept the beam, and to exit from the housing means. The apparatus further comprises a means for closing the apertures and a means for purging said gas from the housing means.

A method of using such a gas measuring apparatus comprises emitting said beam of radiation with the gas in the housing means. The amount of radiation received by the detector is measured. The apertures of the housing means are closed. The gas is purged from the housing means. The amount of radiation received by the detector is determined. The amount of gas in the housing means is calculated based upon the amount of radiation measured and the amount of radiation determined.

BRIEF DESCRIPTION OF THE DRAWINGS

FIG. 1 is a side view of the gas measuring apparatus of the present invention.

FIG. 2A is a cross-sectional view of FIG. 1 taken along the plane 2—2, showing the apertures of the apparatus of the present invention, open.

FIG. 2B is a cross-sectional view of FIG. 1 taken along the plane 2—2, showing the apertures of the apparatus of the present invention, closed.

FIG. 3 is a pictorial view of the use of the apparatus of the present invention in a stack to monitor the exhaust gas from the combustion.

FIG. 4 is a graph of the absorption spectrum of a typical gas as a function of the frequency.

DETAILED DESCRIPTION OF THE DRAWINGS

Referring to FIG. 1 there is shown a gas measuring apparatus 10 of the present invention. The gas measuring apparatus 10 comprises a first enclosure 12, a second enclosure 14 and a first tube 16. The first tube 16 is hollow inside. The first enclosure 12 is to one side of the first tube 16 while the second enclosure 14 is to the other side of the first tube 16. Within the first tube 16 is a second tube 18. The second tube 18 is also hollow inside. A source 20 is in the first enclosure 12. The source 20 is capable of emitting a beam 22 of radiation (shown as dash-dot-dash line). The beam 22 is aligned, to pass through inside the second tube 18 which is inside the first tube 16, and to impinge a detector 24 in the second enclosure 14. The first tube 16 and the second tube 18 both enclose the beam 22. The first tube 16 has a plurality of apertures (only 26a and 26b are shown). The apertures 26a and 26b are located on opposite sides of the first tube 16; they permit gas to enter the first tube 16 via one aperture, e.g. 26b, to intercept the beam 22, and to exit via another aperture, e.g. 26a. The second tube 18 within the first tube 16 serves to control the entry of gas into the first tube 16 to intercept the beam 22. Shown in FIG. 2A, the second tube 18 also comprises a plurality of apertures (only 28a and 28b are shown). In the position shown in FIG. 2A, the apertures 28a and 28b of the second tube 18 are substantially aligned with two of the apertures, 26a and 26b, of the first tube 16, permitting the gas to enter the first tube 16 and second tube 18, to intercept the beam 22 and to exit from the second tube 18 and first tube 16. The second tube 18 is capable of being rotated by, for example, a motor 30. In the position shown in FIG. 2B, the second tube 18 closes substantially all the apertures of the first tube 16 and intercepting the beam 22. Blowers 32a and 32b are provided to purge the gas from the inside of second tube 18.

In general, any housing means can be used to enclose the beam 22. Any closing means can be used to close the apertures 26a and 26b of the first tube 16.

One use of the apparatus 10 of the present invention is in monitoring the exhaust gas 34 of combustion from a stack 36, shown in FIG. 3. Typically, the first enclosure 12 and the second enclosure 14 are on opposite sides of the stack 36, with the first tube 16 passing through the stack 36. In such application, the apparatus 10 is useful for monitoring the exhaust gas 34 to insure compliance with applicable environmental standards, such as the EPA. In such application, the apparatus 10 may operate as an opacity sensor, with the source 20 emitting a beam 22 of visible light.

In the method of the present invention, the source 20 emits a beam 22 of radiation at a frequency (shown as $\nu_1$ in FIG. 4) which is absorbed by the gas 34. The beam 22 passes through the gas 34 in the second tube 18 and is absorbed as it travels to the detector 24. The intensity of the beam 22, received by the detector 24, is dependent upon the amount of absorption, i.e. the greater the absorption, the lower the intensity of the beam 22 received by the detector 24, and vice versa. This is shown as $I_3$ in FIG. 4. The apertures 26a and 26b of the first tube 16 are then closed by for example the motor 30 rotating second tube 18. The gas 34 is purged from the second tube 18 by the blowers 32a and 32b. The gas 34 is replaced by a gas, such as atmospheric gas, which permits substantially all of the beam 22 of radiation at a frequency $\nu_1$ to pass without an absorption. The detector 24 measures the radiation after the beam 22 passes through the second tube 18, unimpeded by the gas 34. This is shown as $I_1$ in FIG. 4. The amount of gas 34 that was in the second tube 18 is calculated based upon $I_1$ and $I_3$ in accordance with Beer's law, i.e.

$$I_3 = I_1 e^{-\mu cL} \text{ or } c = \frac{1}{\mu L} \text{Ln} \frac{I_1}{I_3}$$

where
- $\mu$—absorption coefficient (1/ppm—cm)
- c—concentration of gas (ppm)
- L—path length in gas (cm)

Typically, the frequency $\nu_1$ is in the infrared region and the curve shown in FIG. 4 is the absorption band of carbon dioxide. The advantage of the apparatus and method of the present invention is that the reference measurement (i.e. the measurement made without absorption by the gas 34) is performed under substantially the same condition as the measurement with the gas 34. Except for the removal of the gas 34 the reference measurement uses the same source and electronics, follows the same optical path and is subject to the same environment as the measurement made with the gas 34. This provides for greater accuracy and reliability than has been achieved heretofore.

Heretofore, because it has not been possible to make a measurement with the gas 34 and a measurement without the gas 34, measurements were made based upon a beam of radiation at two different frequencies—one which is absorbed by the gas 34 and another which is not absorbed. In the method of the prior art, the source 20 emits a beam 22 of radiation at a first frequency $\nu_1$ which is absorbed by the gas 34 and a second frequency $\nu_2$ which is not absorbed by the gas 34. The detector 24 receives the beam 22 after it passes through the gas 34. The detector 24 measures the amount of first frequency $\nu_1$ received, i.e. $I_3$, and measures the amount of second frequency $\nu_2$ received, i.e. $I_2$. Calculation of the amount of gas 34 in the first tube 16 is made based upon $I_2$ and $I_3$ in accordance with Beer's law, based upon the assumption that $I_2$ is the same as $I_1$. However, it should be noted from FIG. 4, that even though the second frequency $\nu_2$ is chosen such that it is not absorbed by the gas 34, the amount of second frequency $\nu_2$ received may not be exactly the same as the amount of first frequency $\nu_1$ received but without the gas 34 in the first tube 16, i.e. $I_2$ may not necessarily be exactly the same as $I_1$. There are many possible causes for this, including drift in electronics, since $\nu_2$ is a frequency different from $\nu_1$. This is clearly a source of error.

In another method of the present invention, this error is eliminated by standardizing the value of $I_2$, i.e. determining the quantitative relationship between $I_2$ and $I_1$. To standardize the value of $I_2$, the apertures 26a and 26b of the first tube 16 are closed. The gas 34 is removed from the second tube 18. The source 20 emits a beam of radiation at a first frequency $\nu_1$ which is absorbed by the gas 34 and a second frequency $\nu_2$ which is not absorbed by the gas 34. The detector 24 measures the amount of radiation received at first frequency $\nu_1$ (i.e. $I_1$) and the amount of radiation received at a second frequency $\nu_2$ (i.e. $I_2$). A standardization factor based upon $I_1$ and $I_2$ is determined, i.e.

$$K = I_1/I_2$$

Thereafter, in the measurement of the amount of gas 34 in the first tube 16 using a first frequency $\nu_1$ and a second frequency $\nu_2$, the calculation of the amount of gas 34 that was in the first tube 16 is based upon $I_3$, $I_2$ and K in accordance with $$I_3 = KI_2 e^{-\mu cL} \text{ or } c = \frac{1}{\mu L} \text{Ln} \frac{KI_2}{I_3}$$

where $\mu$, c and L are as previously discussed. In this method, the first tube 16 need not be closed upon every measurement. Instead, the closing of the first tube 16 is used to standardize the apparatus 10 and to correlate $I_2$ to $I_1$.

What is claimed is:

1. A gas analyzer capable of measuring select properties of exhaust gas of combustion, said exhaust gas having a direction of flow in a stream and flowing through a stack, said analyzer with standardization means, comprising:
   a source located to one side of said stack and capable of emitting a beam of radiation;
   said beam aligned to pass substantially through said stream at a direction substantially perpendicular to the direction of flow of said stream;
   a detector, aligned to receive said beam after passing substantially through said stream;
   housing means for enclosing said beam, said means having at least two apertures permitting said gas to enter said means, to intercept said beam, and to exit from said means;
   a member within said housing means and enclosing said beam;
   said member having a plurality of apertures;
   rotating means capable of aligning the apertures of said housing means and the apertures of said member such that a plurality of the apertures of said member are substantially aligned with at least two apertures of said housing means to permit said gas to enter said member, to intercept said beam, and to exit from said member;
   said rotating means also capable of aligning the apertures of said housing means and the apertures of said member to prevent said gas from entering said member; and
   means for purging said gas from said housing means.

2. The apparatus of claim 1 wherein said housing means is substantially tubular in shape.

3. The apparatus of claim 2 wherein said member is substantially tubular in shape.

4. A method of standardizing a gas analyzer capable of measuring select properties of exhaust gas of combustion, said exhaust gas having a direction of flow in a stream and flowing through a stack, said apparatus having a source located to one side of said stack and capable of emitting a beam of radiation at a first frequency which is absorbed by said gas and a second frequency which is not absorbed by said gas; said beam aligned to pass substantially through said stream at a direction substantially perpendicular to the direction of flow of said stream; a detector aligned to receive said beam after passing substantially through said stream; housing means for enclosing said beam, said means having at least two apertures permitting said gas to enter said means, to intercept said beam and to exit from said means; a member within said housing means and enclosing said beam; said member having a plurality of apertures; rotating means capable of aligning the apertures of said housing means and the apertures of said member such that a plurality of the apertures of said member are substantially aligned with at least two apertures of said housing means to permit said gas to enter said member, to intercept said beam, and to exit from said member; said rotating means also capable of aligning the apertures of said housing means and the apertures of said member to prevent said gas from entering said member; means for purging said gas from said housing means, said method comprising:

aligning the apertures of said housing means and the apertures of said member to prevent gas from entering said member;

purging said gas from said housing means;

emitting said beam of radiation;

measuring the amount of radiation at said first frequency received by said detector;

determining the amount of radiation at said second frequency received by said detector; and standardizing said apparatus based upon said first frequency measured and said second frequency determined.

5. The method of claim 4 wherein said standardization step further comprises:

dividing the first frequency determined by the second frequency measured.

* * * * *